(12) United States Patent
Choi et al.

(10) Patent No.: US 8,835,503 B2
(45) Date of Patent: Sep. 16, 2014

(54) PHARMACEUTICAL COMPOSITION CONTAINING GLUR2-LACKING AMPAR ANTAGONIST FOR PREVENTING OR TREATING PSYCHIATRIC ILLNESSES

(71) Applicant: SNU R&DB Foundation, Seoul (KR)

(72) Inventors: Sukwoo Choi, Seoul (KR); Sukwon Lee, Seoul (KR); Jeongyeon Kim, Seoul (KR); Beomjong Song, Seoul (KR); Ingie Hong, Seoul (KR); Sungmo Park, Bucheon-si (KR); Jihye Kim, Seoul (KR); Junuk Lee, Seoul (KR); Bobae An, Seongnami-si (KR); Kisoon Shin, Seoul (KR); Kyungjoon Park, Seoul (KR)

(73) Assignee: SNU R&DB Foundation, Seoul (KR)

( * ) Notice: Subject to any disclaimer, the term of this patent is extended or adjusted under 35 U.S.C. 154(b) by 0 days.

(21) Appl. No.: 13/658,899

(22) Filed: Oct. 24, 2012

(65) Prior Publication Data
US 2013/0046023 A1 Feb. 21, 2013

Related U.S. Application Data

(62) Division of application No. 12/996,751, filed as application No. PCT/KR2009/000669 on Feb. 12, 2009.

(51) Int. Cl.
*A61K 31/37* (2006.01)
*A61K 31/137* (2006.01)

(52) U.S. Cl.
CPC .................................... *A61K 31/137* (2013.01)
USPC .......................................... 514/617; 514/657

(58) Field of Classification Search
CPC . A61K 31/135; A61K 31/136; A61K 31/137; A61K 31/138; A61K 31/165
See application file for complete search history.

(56) References Cited

U.S. PATENT DOCUMENTS 5,544,872 A  8/1996 Schuit

FOREIGN PATENT DOCUMENTS

| DE | 4239816 A1 | 6/1994 |
| KR | 10-1999-022588 A | 3/1999 |
| WO | 94/07914 A1 | 4/1994 |

OTHER PUBLICATIONS

Bisson ("Pharmacological treatment of post-traumatic stress disorder," Advances in Psychiatric Treatment, vol. 13, pp. 119-126, 2007).*
Merck Manual for Health Care Professionals, updated Jul. 2012 (http://www.merckmanuals.com/professional/psychiatric_disorders/anxiety_disorders/phobic_disorders.html#v1025736).*
Steckler et al. ("Pharmacological treatment of PTSD—Established and new approaches," Neuropharmacology, vol. 62, pp. 617-627, 2012).*
Camera et al. ("Systemic administration of polyaminergic agents modulate fear conditioning in rats," Psychopharmacology, vol. 192, pp. 457-464, 2007).*
Washburn et al. ("Block of alpha-Amino—3-hydroxy-5-methyl-4-isoxazolepropionic Acid (AMPA) Receptors by Polyamines and Polyamine Toxins," The Journal of Pharmacology and Experimental Therapeutics, vol. 278, pp. 669-678, 1996).*
Szinyei et al. ("Plasticity of inhibitory synaptic network interactions in the lateral amygdala upon fear conditioning in mice." European Journal of Neuroscience, vol. 25, pp. 1205-1211, 2007).*
Yoneda et al. ("Discovery of Diaminobutane Derivatives as Ca2+-Permeable AMPA Receptor Antagonists," Bioorganic and Medicinal Chemistry, vol. 10, pp. 1347-1359, 2002).*
European Patent Office, European Search Report issued in corresponding EP Application No. 09840060.9, dated Jul. 18, 2012.
Ozawa et al., "Glutamate Receptors in the Mammalian Central Nervous System," Progress in Neurobiology, 1998, vol. 54, No. 5, pp. 581-618.
Conrad et al., "Formation of Accumbens GluR2-lacking AMPA Receptors Mediates Incubation of Cocaine Craving," Nature, 2008, vol. 454, pp. 118-124.
Rao et al., "NMDA and AMPA Receptors: Old Channels, New Tricks," Trends in Neurosciences, 2007, vol. 30, No. 6, pp. 284-291.
Bellone et al., "Cocaine Triggered AMPA Receptor Redistribution in Reversed in vivo by mGluR-dependent Long-Term Depression," Nature Neuroscience, 2006, vol. 9, No. 5, pp. 636-641.
Zushida et al., "Facilitation of Extinction Learning for Contextual Fear Memory by PEPA: A Potentiator of AMPA Receptors," The Journal of Neuroscience, 2007, vol. 27, No. 1, pp. 158-166.
Sepehrizadeh et al., "Decreased AMPA GLuR2, but not GLuR3, Mrna Expression in Rat Amygdala and Dorsal Hippocampus Following Morphine-Induced Behavioral Sensitization", Clin Exp. Pharmacol Physiol. Nov. 2008, 1 page vol. 35, No. 11.
Da Cunha, IC, "The microinjection of AMPA receptor antagonist into the accumbens shell failed to change food intake, but reduced fear-motivated behavior in free-feeding female rats", Behav Brain Res. 21, Nov. 2008, 1 page, vol. 193, No. 2.
Katie R. Famous, "Phosphorylation-Dependent Trafficking of GluR2-Containing AMPA Receptors in the Nucleus Accumbens Plays a Critical Role in the Reinstatement of Cocaine Seeking", The Journal of Neuroscience, Oct. 22, 2008, pp. 11061-11070, vol. 28, No. 43.
Washburn et al., "Block of alpha-Amino-3-hydroxy-5-methyl-4-isoxazolepropionic Acid (AMPA) Receptors by Polyamines and Polyamine Toxins," J. Pharm. Therap., 1996, vol. 278, No. 2, pp. 669-678.
Yoneda et al., "Discovery of Diaminobutane Derivatives as $Ca^{2+}$-Permeable AMPA Receptor Antagonists," Bioorganic Medicinal Chemistry, 2002, vol. 10, No. 5, pp. 1347-1359.
Muller et al., "Functional Inactivation of the Lateral and Basal Nuclei of the Amygdala by Muscimol Infusion Prevents Fear Conditioning to an Explicit Conditioned Stimulus and to Contextual Stimuli," Behavioral Neuroscience, 1997, vol. 111, No. 4, pp. 683-691.

* cited by examiner

*Primary Examiner* — Christina Bradley
(74) *Attorney, Agent, or Firm* — Sughrue Mion, PLLC

(57) ABSTRACT

A pharmaceutical composition, comprising a GluR2-lacking AMPAR antagonist as an active ingredient, is effective for preventing or treating mental diseases selected from the group consisting of posttraumatic stress disorder (PTSD), drug addiction, and phobia.

2 Claims, 3 Drawing Sheets

PHARMACEUTICAL COMPOSITION CONTAINING GLUR2-LACKING AMPAR ANTAGONIST FOR PREVENTING OR TREATING PSYCHIATRIC ILLNESSES

CROSS-REFERENCE TO RELATED APPLICATIONS

This application is divisional of U.S. patent application Ser. No. 12/996,751 filed on Dec. 7, 2010, which is a National Stage of International Application No. PCT/KR2009/000669 filed Feb. 12, 2009, the contents of all of which are incorporated herein by reference in their entirety.

FIELD OF THE INVENTION

The present invention relates to a pharmaceutical composition for preventing or treating mental diseases, comprising a GluR2-lacking AMPAR antagonist as an active ingredient and a use thereof.

BACKGROUND OF THE INVENTION

The treatment of posttraumatic stress disorder (PTSD) has been mostly focused on the alleviation of the symptoms by counseling such as exposure therapy and cognitive restructuring. Although medication therapy is available, only indirect palliatives such as antidepressants are used, which makes it hard to treat critical PTSD patients.

Meanwhile, although there are various methods for treating patients suffering from drug addiction or phobia, repeated memory renewal after the treatment is the most prominent clinical difficulty. Therefore, there exists a need to investigate physiological mechanism of memory renewal for preventing renewal of drug addiction/fear memory.

The α-Amino-3-hydroxy-5-methyl-4-isoxazolepropionic acid receptor (AMPAR) is an ionotropic glutamate receptor that mediates fast synaptic transmission in the central nervous system (CNS). AMPARs are composed of four types of subunits, designated GluR1, GluR2, GluR3, and GluR4. $Ca^{2+}$ permeability of AMPAR depends on the constitution of the subunits, i.e., receptors having GluR2 subunit show low $Ca^{2+}$ permeability while receptors having no GluR2 subunit show high $Ca^{2+}$ permeability (*Trends Neurosci.* 16, 359-365, 1993; *Annu. Rev. Neurosci.* 17, 31-108, 1994; *Prog. Neurobiol.* 54, 581-618, 1998).

GluR2-lacking AMPAR antagonists, mostly derivatives of spermine, have been reported to be useful for treating epilepsy and cerebral infarction (Yoneda et. al., *Bioorg Med Chem.* 11(10), 1261-1264, 2001). However, it has not been reported whether GluR2-lacking AMPAR antagonists may be effective in the treatment of PTSD, drug addiction or phobia.

SUMMARY OF THE INVENTION

It is an object of the present invention to provide a pharmaceutical composition for preventing or treating mental diseases, comprising a GluR2-lacking AMPAR antagonist as an active ingredient.

There is provided a pharmaceutical composition for preventing or treating mental diseases selected from the group consisting of posttraumatic stress disorder (PTSD), drug addiction, and phobia, comprising a GluR2-lacking AMPAR antagonist as an active ingredient.

Further, it is another object of the present invention to provide a use of GluR2-lacking AMPAR antagonists for preventing or treating mental diseases selected from the group consisting of PTSD, drug addiction, and phobia in a subject.

A pharmaceutical composition comprising a GluR2-lacking AMPAR antagonist as an active ingredient is useful for preventing or treating mental diseases in a subject since the antagonist prevents the necrosis of brain cells by inhibiting accumulation of calcium ($Ca^{2+}$), zinc ($Zn^{2+}$), etc. in the neurons and reduces neural activity of the corresponding brain regions related to the disease.

BRIEF DESCRIPTION OF THE DRAWINGS

The above and other objects and features of the present invention will become apparent from the following description of the invention, when taken in conjunction with the accompanying drawings, which respectively show that.

DETAILED DESCRIPTION OF THE INVENTION

Figure 1:
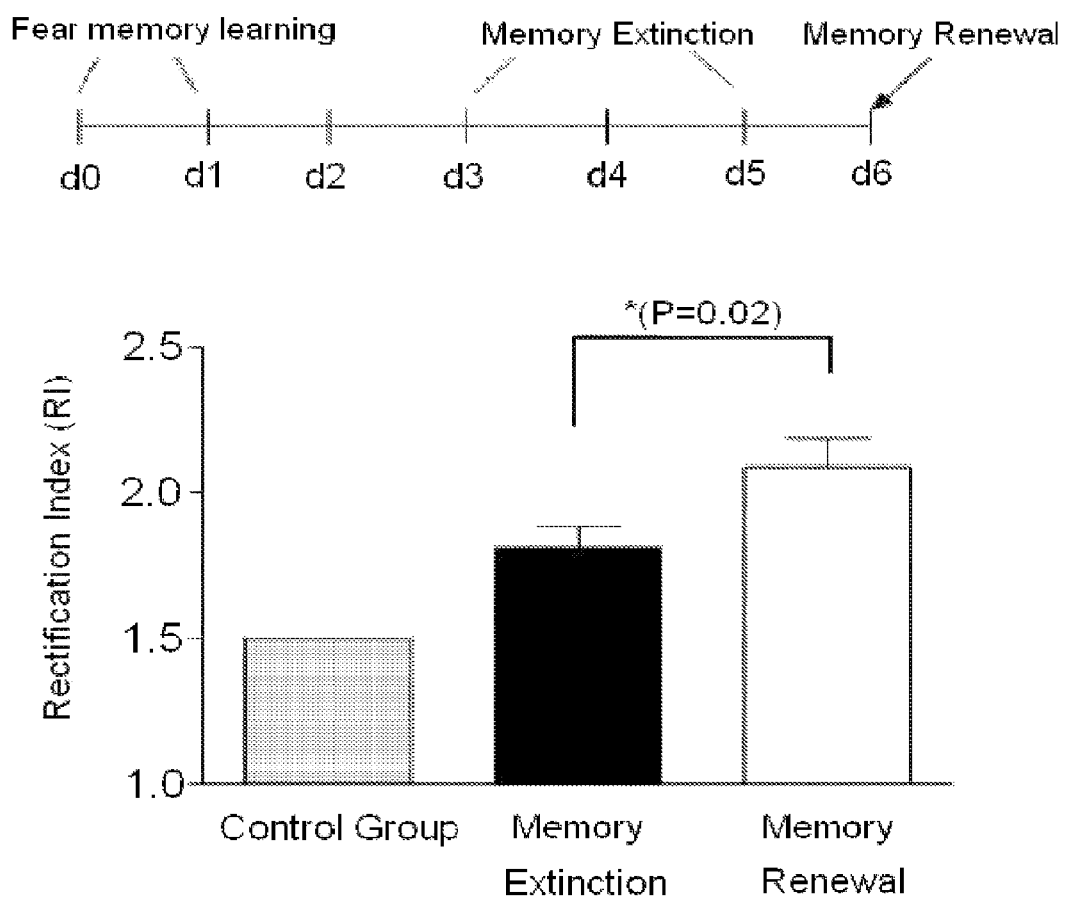
FIG. 1: GluR2-lacking AMPAR accumulation in the amygdala synapse by repeated retrieval of fear memory.

The pharmaceutical composition of the present invention for preventing or treating mental diseases comprises a GluR2-lacking AMPAR antagonist as an active ingredient.

The mental diseases include posttraumatic stress disorder (PTSD), drug addiction, and phobia.

The composition of the present invention comprising a GluR2-lacking AMPAR antagonist as an active ingredient prevents the necrosis of brain cells by inhibiting the accumulation of calcium ($Ca^{2+}$), zinc ($Zn^{2+}$), etc. in the neurons and reduces neural activity of the corresponding brain regions related to the disease, thereby suppressing the underlying behaviors of the mental diseases such as PTSD, drug addiction, and phobia.

The GluR2-lacking AMPAR antagonist may be N-naphthylspermine (NASPM), philanthotoxin, Joro spider toxin or N-(4-hydroxyphenylpropanoyl)-spermine (NHPP-spermine).

Further, the composition of the present invention comprising the GluR2-lacking AMPAR antagonist may further comprise other ingredients such as vitamins, minerals, and blood circulation improving agents.

Examples of suitable vitamins include vitamin B1, B2, B6, B12, C, calcium pantothenate, nicotinamide, folic acid, and biotin.

Examples of suitable minerals include zinc, iron, calcium, and magnesium.

It is preferred to employ the vitamins and minerals in combination for enhancing their biological activities. Preferably, a vitamin or a mineral may be included in the composition in an amount of 0.1 to 10 wt % based on the total weight of the composition. More preferably, vitamin B 1, B2, and C may be included in amounts of 0.01 to 3 wt %, 0.01 to 3 wt %, and 0.01 to 4 wt %, respectively, based on the total weight of the composition.

Examples of suitable blood circulation improving agents are gamma-linolenic acid, EPA, and tocopherol.

The blood circulation improving agents may be employed in combination in order to enhance the blood circulation effect and biological activities. Preferably, the blood circulation improving agent is tocopherol, and it may be used in an amount of 5 to 30 wt % based on the total weight of the composition.

Further, the composition of the present invention may further comprise a solvent which is capable of dissolving all the ingredients including the GluR2-lacking AMPAR antagonist, vitamins, minerals, and blood circulation improving agents. Examples of suitable solvents are water and ethyl alcohol.

Meanwhile, the composition of the present invention is preferably processed into pharmaceutical preparations, together with a pharmaceutically acceptable carrier, in accordance with the conventional medicament preparation methods. Examples of suitable carriers are lactose, dextrose, sucrose, sorbitol, mannitol, xylitol, erythritol, maltitol, starch, gum acacia, alginate, gelatin, calcium phosphate, calcium silicate, cellulose, methyl cellulose, microcrystalline cellulose, polyvinylpyrrolidone, water, methyl hydroxybenzoate, propyl hydroxybenzoate, talc, magnesium stearate, and a mineral oil.

Further, the composition of the present invention may further comprise fillers, anti-agglomerating agents, lubricating agents, wetting agents, flavoring agents, emulsifiers or preservatives.

The composition of the present invention may be formulated so as to provide a quick, sustained or delayed release of the active ingredient after administration to a subject by any of the known methods. The formulation may be in the form of a tablet, pill, granule, powder, sachet, elixir, suspension, emulsion, solution, syrup, aerosol, soft and hard gelatin capsule, sterile injectable solution, sterile packaged powder, and others. In the preparation of the formulation such as a granule and liquid, it may be desirable to add thereto a natural flavoring agent or natural juice having the flavor of plum, lemon, pineapple or herb, a natural coloring agent such as chlorophyllin, a sweetening agent such as fructose, honey, sugar alcohol, sucrose or an acidifier such as citric acid and sodium citrate.

Further, the composition of the present invention can be administrated by various routes such as oral administration or injection.

An effective daily dose of the composition of the present invention may range from about 0.01 to 20 g/kg. However, it should be understood that the amount of the active ingredient actually administered ought to be determined in consideration of various relevant factors including the age, sex, the weight of the patient to be treated, and the severity of the symptom of the disease. The daily dose should not be intended to limit the scope of the invention in any way.

Further, the present invention also provides a use of GluR2-lacking AMPAR antagonist for preventing or treating mental diseases selected from the group consisting of PTSD, drug addiction, and phobia in a subject.

The subject may be a mammal, e.g., human.

The GluR2-lacking AMPAR antagonist may be N-naphthylspermine (NASPM), philanthotoxin, Joro spider toxin or N-(4-hydroxyphenylpropanoyl)-spermine (NHPP-spermine).

The following Examples are intended to further illustrate the present invention without limiting its scope.

EXAMPLE 1

Accumulation of GluR2-Lacking AMPAR in the Amygdala Synapse by Repeated Retrieval of Fear Memory Tests were conducted to examine whether GluR2-lacking AMPAR accumulates in the amygdala synapse by repeated retrieval of fear memory.

EXAMPLE 1-1

Fear Memory Learning, Memory Extinction, and Memory Renewal

White rats, 4-5 weeks old (Sprague-Dawley Rat, Male; Orient Bio Inc., Korea) were used in the following experiments. All rats were kept while allowing free access to food and water under a 12 hour cycle of light and dark (the light was turned off at 9 am).

For fear memory learning, the rats were exposed to sound stimuli of a single tone (2.8 kHz, 85 dB) for 30 seconds, and subjected to an electric foot shock (1.0 mA) for 1 second at the end of said 30-second period. The sound stimuli and the electric foot shock were repeated 3 times at 100 second intervals. 1 minute later after the last electric foot shock, the rats were returned to their home cages. On day 2, fear memory learning was performed in the same way.

From day 3, memory extinction was performed in a context different from that of the fear memory learning On day 4, the rats were exposed to only sound stimuli 20 times at 100 second intervals without an electric foot shock. On days 5 and 6, the sound stimuli were repeated 15 times at 100 second intervals.

On day 7, memory renewal test was performed. The rats experienced memory extinction were placed in the place of the fear memory learning for 10 minutes, and then, memory renewal was induced by exposing the rats to sound stimuli for 30 seconds.

EXAMPLE 1-2

Preparation of Brain Slices

The brains of the rats of the group of memory extinction and memory renewal were extracted and placed in a modified artificial cerebrospinal fluid (aCSF). The composition of the modified artificial cerebrospinal fluid used was as follows: 175 mM sucrose, 20 mM NaCl, 3.5 mM KCl, 1.25 mM $NaH_2PO_4$, 26 mM $NaHCO_3$, 1.3 mM $MgCl_2$, and 11 mM D-(+)-glucose (Sigma-Aldrich Co., USA). About 3 minutes later, the brains were sliced into 0.3 mm thick slices using a vibroslicer (HA752, Campdem Instruments, Loughborough, UK). The brain slices containing amygdala were cultured in a artificial cerebrospinal fluid (120 mM NaCl, 3.5 mM KCl, 1.25 mM $NaH_2PO_4$, 26 mM $NaHCO_3$, 1.3 mM $MgCl_2$, 2 mM $CaCl_2$, 11 mM D-(+)-glucose) containing 95% $O_2$/5% $CO_2$ at room temperature for over 1 hour. The cortex overlying the amygdala was removed just before taking it to the equipment for measuring the synaptic reaction.

EXAMPLE 1-3

Measurement of Synaptic Efficacy Using Whole-Cell Patch-Clamp

Synaptic responses were measured in 32-34° C. artificial cerebrospinal fluid using Axopatch 200A or Multiclamp 700A (Molecular Devices, Calif.). A patch-pipette solution based on potassium (K) was prepared which consisted of the following: 120 mM K-gluconate, 0.2 mM EGTA, 10 mM HEPES, 5 mM NaCl, 1 mM $MgCl_2$, 2 mM Mg-ATP, and 0.3 mM Na-GTP (Sigma-Aldrich Co., USA).

To confirm whether the neuron recorded is a principal neuron, the shape of the cell and spike-frequency adaptation of the action potential induced by a current injection was examined. Picrotoxin (0.1 mM, Sigma-Aldrich Co., USA)

was added to the artificial cerebrospinal fluid to block inhibitory inputs to principal neurons. The pipette resistances ranged from 2.5 to 3.5 Mohm. The pipette series resistance was monitored throughout the experiments, and if it changed by >20% the data were discarded. All the experiments were performed within 3.5 hours after preparing the brain slices.

EXAMPLE 1-4

Measurement of Rectification Index (RI)

The rectification index (RI) was calculated as the ratio of synaptic responses at membrane potentials of −60 mV and +40 mV, which increased as the GluR2-lacking AMPAR accumulates.

The internal solution contained spermine (0.1 mM, Sigma Aldrich Co., USA). The reversal potential (Erev) was measured in each experiment. RI (Erev +40 mV/Erev −60 mV) was compared at 20 minutes after the start of whole-cell recordings to ensure complete diffusion of exogenous spermine into the cell interior, and D-AP5 (Tocris, USA) was applied 5 minutes before the RI estimation to isolate AMPAR-mediated excitatory postsynaptic currents (EPSCs) at positive potentials. The RI at the membrane potentials of −60 mV and 40 mV were measured 6 times, respectively. The average of RI values was used to determine the RI of the neuron.

EXAMPLE 1-5

Results

The rats of the control group which did not experience fear memory learning showed RI of 1.5, which shows that the synaptic response size is in direct proportion to the membrane potential size (Tsvetkov et al., Neuron, Vol. 34, 289-300, Apr. 11, 2002). In comparison, the rats of the experimental groups of memory extinction and memory renewal which experienced repeated retrieval of fear memory showed higher RI values. Further, the rats of memory renewal group showed significantly higher RI values than those of memory extinction group (see FIG. 1). This suggests that GluR2-lacking AMPAR accumulates in the amygdala synapse as fear memory repeats and recurs.

EXAMPLE 2

Suppression of the Synaptic Reaction by GluR2-Lacking AMPAR Antagonist, NASPM 0.3 mm thick brain slices were prepared from the rats which experienced fear memory learning, memory extinction, and memory renewal in accordance with the method described in Examples 1-1 and 1-2.

The thalamic afferent fibers connecting thalamus to the lateral amygdala were stimulated using concentric bipolar electrode (MCE-100, Rhodes Medical Instruments, Calif., USA) in order to induce synaptic responses. In order to examine the basal response value of the amygdala synapse, the size of synaptic response was measured for 10 minutes, 200 μM of NASPM (N-naphthylspermine, Sigma-Aldrich Co., USA) dissolved in a artificial cerebrospinal fluid was administered, and the size of synaptic responses was measured.

Figure 2:
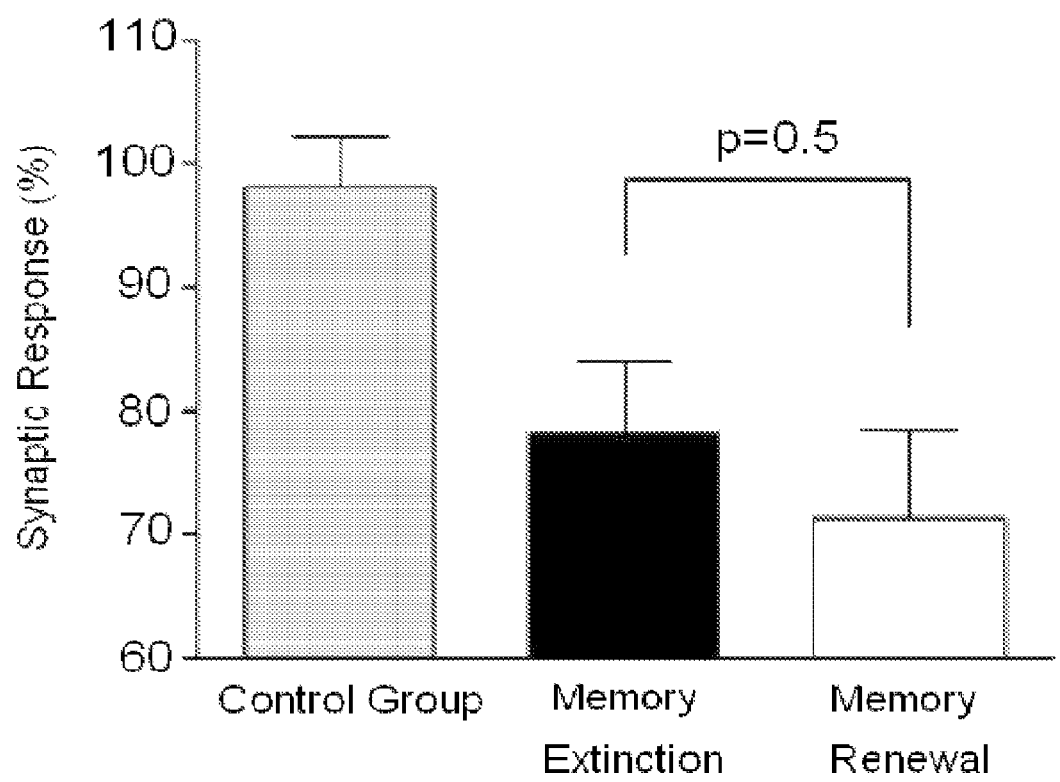
FIG. 2: suppression of amygdala synaptic responses by a GluR2-lacking AMPAR antagonist, NASPM, in the experimental groups of memory extinction and memory renewal.

As a result, the synaptic response of the amygdala was inhibited by 200 μM of NASPM in the experimental groups of memory extinction and memory renewal (see FIG. 2). The results of the control group, obtained by Vadim Bolshakov of Harvard university (Tsvetkov et al., 2002), show that the inhibition by NASPM is subtle in case of the rats which did not experience fear memory learning The result obtained by NASPM proves that GluR2-lacking AMPAR accumulates in the amygdala synapse as fear memory relapses.

EXAMPLE 3

Blocking Effect of Fear Memory Renewal by GluR2-Lacking AMPAR Antagonist, NASPM An in vivo experiment was performed in order to examine whether NASPM administered in the amygdala blocks fear memory renewal.

EXAMPLE 3-1

Fear Memory Learning, Memory Extinction and Memory Renewal

The experiment was performed using the rats which experienced fear memory learning, memory extinction and memory renewal in accordance with the method described in Example 1-1. White rats, 8-9 weeks old (Sprague-Dawley Rat, Male; Samtako, Korea), were used.

EXAMPLE 3-2

Administration of NASPM

The rats were anesthetized by intraperitoneal injection of pentobarbital sodium (50 mg/kg; Entobal, Hanlim Pharma, Co., Ltd., Korea). After fully anesthetized, the rats were mounted on a stereotaxic apparatus (David Kopf Instruments, Tujunga, Calif., USA), and then, stainless steel cannulas of 26 gauge (Model C315G, Plastic Products, Roanoke, Va., USA) were implanted bilaterally into the amygdala (AP; −0.3 mm, ML; +/−5.15, DV; −7.0 mm) by operation. A 32 gauge dummy cannula was inserted into each cannula to prevent clogging. After a recovery period of at least 1 week, the rats were subjected to fear memory learning, memory extinction and memory renewal tests. Then, the brain slices of 0.08 mm thickness were prepared and stained with cresyl violet (Sigma-Aldrich Co., USA) cannula in order to confirm whether the cannulas were exactly implanted in the amygdalas. 40 μg and 10 μg of NASPM (Sigma-Aldrich Co., USA) were respectively dissolved in 0.0005 ml of normal saline, and then, the solutions were respectively administered to the rats using a 0.01 ml hamilton syringe at a rate of 0.00025 ml/min through said cannulas, 15 minutes before measuring fear memory.

EXAMPLE 3-3

Measurement of the Fear Reaction

The duration that the rats showed freezing response while exposed to the sound stimuli was measured in order to examine remaining memory (Kim et. al., PNAS, 104(52), 20955-20960, 2007). Conditioned freezing was defined as immobility except for respiratory movements, and was quantified by trained observers that were blind to the experimental groups.

EXAMPLE 3-4

Results

Figure 3:
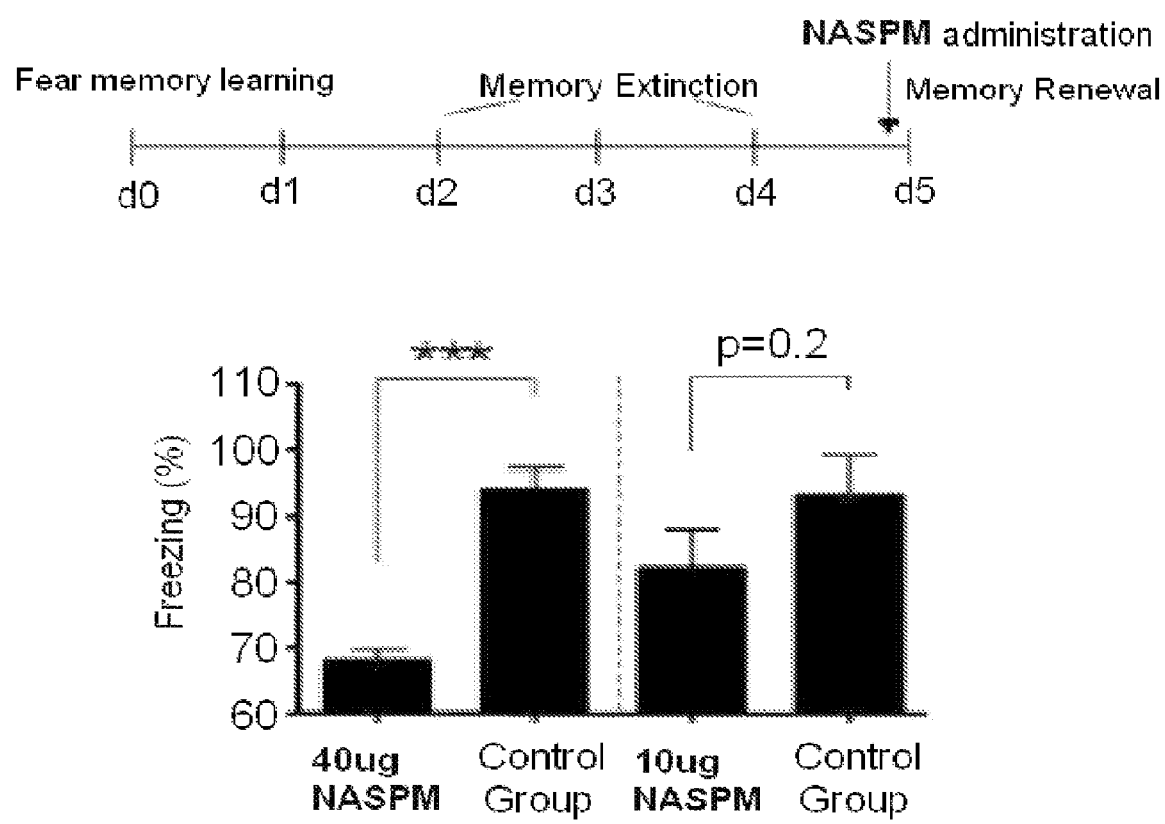
FIG. 3: concentration-dependent blocking of the renewal of fear memory by the administration of a GluR2-lacking AMPAR antagonist, NASPM, into the amygdala.

In comparison with the control group, the experimental group administered with 40 μg of NASPM, a GluR2-lacking AMPAR antagonist, showed a remarkably less fear responses, while the group administered with 10 µg of NASPM showed an insignificant effect (see FIG. 3). These results show that GluR2-lacking AMPAR accumulated in amygdala synapses by the repeated fear memory recall plays an important role in fear memory renewal. In addition, NASPM, a GluR2-lacking AMPAR antagonist, blocks the fear memory renewal in a concentration-dependent manner, when administered in the amygdala.

While the invention has been described with respect to the above specific embodiments, it should be recognized that various modifications and changes may be made to the invention by those skilled in the art which also fall within the scope of the invention as defined by the appended claims.

What is claimed is:

1. A method of treating a mental disease selected from the group consisting of posttraumatic stress disorder and phobia, comprising administering an effective amount of GluR2-lacking α-Amino-3-hydroxy-5-methyl-4-isoxazolepropionic acid receptor (AMPAR) antagonist to a subject in need thereof, wherein said GluR2- lacking AMPAR antagonist is selected from the group consisting of 1-naphthylacetylspermine, and N-(4-hydroxyphenylpropanoyl)-spermine.

2. The method of claim 1, wherein the mental disease is posttraumatic stress disorder.

* * * * *